United States Patent
Hur

(10) Patent No.: US 10,709,593 B2
(45) Date of Patent: Jul. 14, 2020

(54) KNEE PAIN TREATMENT APPARATUS AND METHOD OF USE

(71) Applicant: Gene Hur, Zionsville, IN (US)

(72) Inventor: Gene Hur, Zionsville, IN (US)

( * ) Notice: Subject to any disclaimer, the term of this patent is extended or adjusted under 35 U.S.C. 154(b) by 1059 days.

(21) Appl. No.: 14/937,964

(22) Filed: Nov. 11, 2015

(65) Prior Publication Data

US 2017/0128248 A1     May 11, 2017

(51) Int. Cl.
    *A61F 5/01*     (2006.01)

(52) U.S. Cl.
    CPC .................. *A61F 5/0109* (2013.01)

(58) Field of Classification Search
CPC ...... A61F 5/058; A61F 5/0585; A61F 5/0123; A61F 5/0109; A61F 5/01; A61F 5/0104; A61F 5/0106; A61F 5/0118; A61F 13/061; A61F 13/062; A61F 5/0111; A41D 13/0543; A41D 13/06; A41D 13/065; A63B 71/12258; A61H 1/024
USPC ............................ 602/26, 5, 23, 62; 128/882
See application file for complete search history.

(56) References Cited

U.S. PATENT DOCUMENTS

| | | | |
|---|---|---|---|
| 1,601,659 A | 9/1926 | Van Harlingen | |
| 2,195,024 A | 3/1940 | Bullock | |
| 3,074,400 A | 1/1963 | Schulman | |
| 4,116,236 A | 9/1978 | Albert | |
| 4,201,203 A | 5/1980 | Applegate | |
| D259,058 S | 4/1981 | Marshall | |
| 4,287,885 A | 9/1981 | Applegate | |
| 4,296,744 A | 10/1981 | Palumbo | |
| 4,366,813 A | 1/1983 | Nelson | |
| 4,370,978 A | 2/1983 | Palumbo | |
| 4,466,428 A | 8/1984 | McCoy | |
| 4,607,628 A | 8/1986 | Dashefsky | |

(Continued)

FOREIGN PATENT DOCUMENTS

| | | | | |
|---|---|---|---|---|
| EP | 0860153 A1 | * | 8/1998 | ........... A61F 5/0106 |
| EP | 0860153 A1 | * | 8/1998 | ........... A61F 5/0106 |

OTHER PUBLICATIONS

EP0860153A1_translation.PDF; english language translation of EP 0860153 A1.*

(Continued)

*Primary Examiner* — Anna K Kinsaul
*Assistant Examiner* — Caitlin A Carreiro
(74) *Attorney, Agent, or Firm* — Maginot, Moore & Beck, LLP

(57) ABSTRACT

The knee pain treatment apparatus includes an upper member constructed to encircle a leg above a knee. The upper member includes an outer surface, an inner surface, an opening for exposing a front of the knee and a tensioning member integral with the upper member and depending downwardly therefrom. A patella biasing device is secured on the inner surface of the upper member and is arranged and constructed to border the opening. The apparatus further includes a flexible lower member arranged and constructed to encircle the leg below the knee and at least one tensioning member fastening system. The tensioning member fastening system is arranged and constructed for connecting the upper member and the lower member. When the upper member and lower member are mounted on the leg and connected, the at least one tensioning member is stretched creating a downward biasing of the patella.

16 Claims, 3 Drawing Sheets

(56) References Cited

U.S. PATENT DOCUMENTS

| | | | |
|---|---|---|---|
| 4,777,946 A | 10/1988 | Watanabe et al. | |
| 4,872,448 A | 10/1989 | Johnson, Jr. | |
| 5,016,621 A * | 5/1991 | Bender | A61F 5/0109 2/22 |
| 5,277,697 A | 1/1994 | France et al. | |
| 5,417,646 A | 5/1995 | Gauvry | |
| 5,514,082 A | 5/1996 | Smith, III | |
| 5,759,167 A | 6/1998 | Shields, Jr. et al. | |
| 5,797,864 A * | 8/1998 | Taylor | A61F 5/0109 128/898 |
| 5,865,776 A | 2/1999 | Springs | |
| 5,873,848 A * | 2/1999 | Fulkerson | A61F 5/0106 602/26 |
| 6,077,242 A | 6/2000 | Falk et al. | |
| 6,080,124 A | 6/2000 | Falk et al. | |
| 6,641,549 B2 | 11/2003 | Darcey | |
| 7,004,919 B2 | 2/2006 | Gaylord et al. | |
| 7,749,181 B2 | 7/2010 | Simmons et al. | |
| 7,862,528 B2 * | 1/2011 | Scott | A61F 5/0106 602/23 |
| 7,959,590 B2 | 6/2011 | Scott | |
| 9,314,364 B2 * | 4/2016 | Nelson | A61F 5/0106 |
| 2004/0153017 A1 * | 8/2004 | Simmons | A61F 5/0109 602/26 |
| 2004/0167452 A1 | 8/2004 | Mason et al. | |
| 2005/0004499 A1 * | 1/2005 | Bauerfeind | A61F 5/0123 602/26 |
| 2009/0131844 A1 * | 5/2009 | Dean | A61F 5/0125 602/36 |

OTHER PUBLICATIONS

Machine translation of EP0860153.*
machine translation of Ep 0860153 (Year: 2001).*
International Search Report corresponding to international application No. PCT/US2016/62589 dated Feb. 7, 2017 (8 pages).

* cited by examiner

KNEE PAIN TREATMENT APPARATUS AND METHOD OF USE

BACKGROUND

The present disclosure relates to apparatus and methods for addressing certain underlying causes of knee pain. Most prior art knee braces are focused on supporting and stabilizing the knee. Some traditional knee braces claim that the stabilization of the patella will alleviate common forms of knee pain such as from patellofemoral syndrome, tendonitis, Osgood Schlatter's disease, osteoarthritis, patellar dislocation, and other like conditions.

However, many research studies have found that these prior art braces are largely ineffective at providing long term pain relief. Moreover, such prior art braces not only do not provide long term relief from pain, but physical symptoms will typically continue to worsen despite use of prior art knee braces.

One of the major reasons that prior art braces are so ineffective in treating knee pain is the failure to address the true cause of knee pain. When it comes to tendonitis, the common belief is that the patella or quadriceps tendon begins to degenerate from overuse. Thus, many braces are focused on putting pressure on those tendons to instill some relief.

However, the underlying problem is not the tendons themselves, but rather is associated with the muscles that attach to those tendons. When muscles are routinely used, they will have a tendency to tighten and shorten in length. When those muscles are shorter, the passive structures in the connective chain suffer as they have to lengthen to accommodate the muscular force. As a result, those tendons become irritated and "overworked", resulting in knee pain.

Other sources of knee pain are also related to the issue of the "tightened" quadriceps muscle. When the patella is lifted out of its groove by the quadriceps muscle, it will eventually lead to other problems, such as patella femoral syndrome. Patella femoral syndrome is the cause of the start of almost every knee ache or pain. It occurs because the patella no longer rests in its groove where congruent surfaces evenly displace pressure. When the quadriceps muscle becomes shortened or tight, it pulls the patella out of place and forces the patella to rest proximally on the femur. This will inevitably cause achiness and swelling which worsens when the knee is bent while sitting. At 90 degrees of knee bend, this is where the patella will have the most pressure on the bones underneath. Patellar dislocations will also occur frequently, if the quadriceps pulls the patella from its groove. The lateral structures will no longer buttress the patella where it sits, and as a result, will dislocate laterally.

Osteoarthritis in the knee occurs faster in those people who do not stretch their quadriceps muscles because the patella is no longer sitting in its groove and thus rests on non-congruent surfaces. This will result in a faster wear of the cartilaginous cushions underneath the patella which will lead to more bone-on-bone contact.

Osgood-Schlatter's disease may not necessarily occur just from muscle shortening as much as it occurs due to bone lengthening. It occurs because the patella tendon does not stretch, and thus will pull on the bone where a prominent growth will occur. Reduction of stress along the muscles and tendons that attach to that surface will ultimately reduce pain symptoms as well.

The only reason that the condition of "patella alta" or the patella sitting high on the knee has not been more scrutinized is that the diagnostic used to determine patella orientation is the Insall-Salvati ratio, which measures the length of the patella tendon against the overall height of the patella. Because the ratio does not scrutinize the position of the patella, patellar height as a contributing factor to all of these disease processes has not been extensively studied. Instead, lateral displacement of the patella is merely viewed as a contributing cause of pain, or often times, not even recognized as the real issue needing to be addressed.

Moreover, even though prior art braces may rest on the patella, they do not apply any downward force on the patella sufficient to stretch the quadriceps muscle and therefore do not address the underlying cause of knee pain. Therefore, a more effective knee brace for alleviating knee pain is needed.

SUMMARY OF DISCLOSURE

In at least one embodiment, the knee pain treatment apparatus of the present disclosure comprises a flexible upper member arranged and constructed to encircle a leg above a knee. The upper member includes an outer surface, an inner surface and an opening for exposing a front of the knee. The upper member further includes at least one tensioning member integral with the upper member and depending downwardly therefrom. A patella biasing device is secured on the inner surface of the upper member and is arranged and constructed to border the opening.

The apparatus further includes a flexible lower member arranged and constructed to encircle the leg below the knee and at least one tensioning member fastening system. The tensioning member fastening system is arranged and constructed for connecting the upper member and the lower member via the at least one tensioning member such that when the upper member and lower member are mounted on the leg and connected via the at least one tensioning member fastening system, the at least one tensioning member is stretched creating a downward biasing of the patella biasing device.

Another embodiment of the present disclosure is a method of treating knee pain using the apparatus of the present disclosure. Such a method includes the steps of providing a flexible upper member arranged and constructed to encircle a leg above a knee, the upper member having an outer surface, an inner surface and an opening for exposing a front of the knee, at least one tensioning member integral with the upper member and depending downwardly therefrom, and a patella biasing device secured on the inner surface and boarding the opening.

The method further includes providing a flexible lower member arranged and constructed to encircle the leg below the knee and providing a tensioning member fastening system arranged and constructed for connecting the upper member and the lower member via the at least one tensioning member. The method further includes attaching the flexible upper member around the leg such that the opening is positioned to expose the front of the knee and to position the patella biasing device in close proximity to a patella. Another step in the method is to attach the flexible lower member around the leg below the knee.

Once the upper member and lower member are properly mounted on the knee, they are connected by stretching the at least one tensioning member in a downward direction and attaching it to the flexible lower member via the tensioning member fastening system so that when the upper member and lower member are connected, the patella biasing device biases the patella in a downward direction resulting in stretching of a quadriceps muscle.

DETAILED DESCRIPTION

Figure 1:
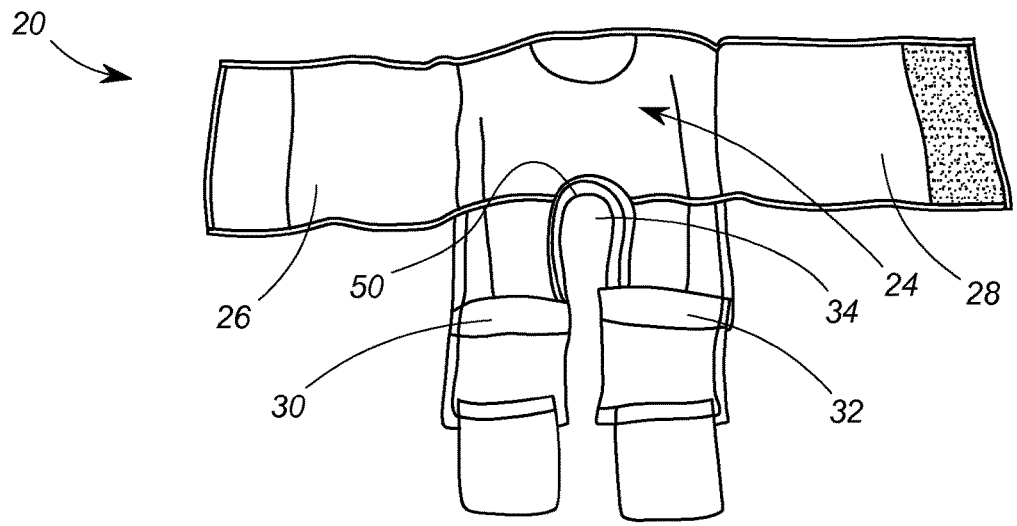
FIG. 1 is a drawing of one aspect of the present disclosure showing an outer view of the upper member of an apparatus for the knee.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

Figure 2:
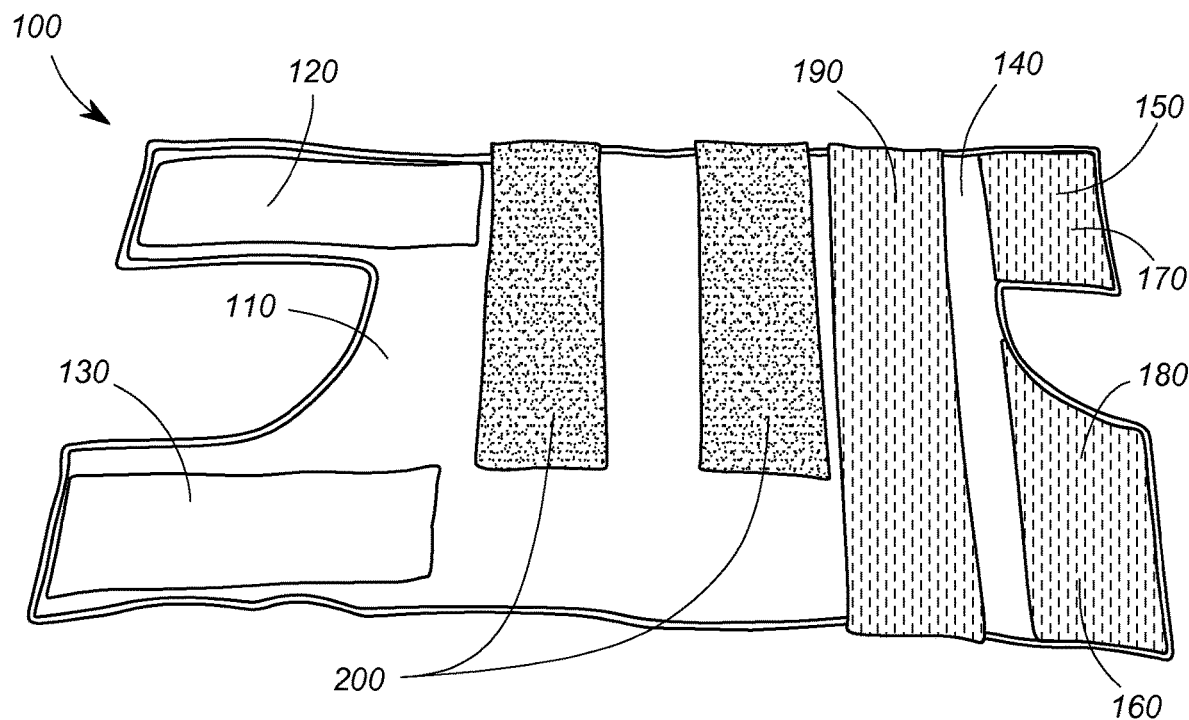
FIG. 2 is a drawing of another aspect of the present disclosure showing an outer view of the lower member of an apparatus for the knee.
Figure 3:
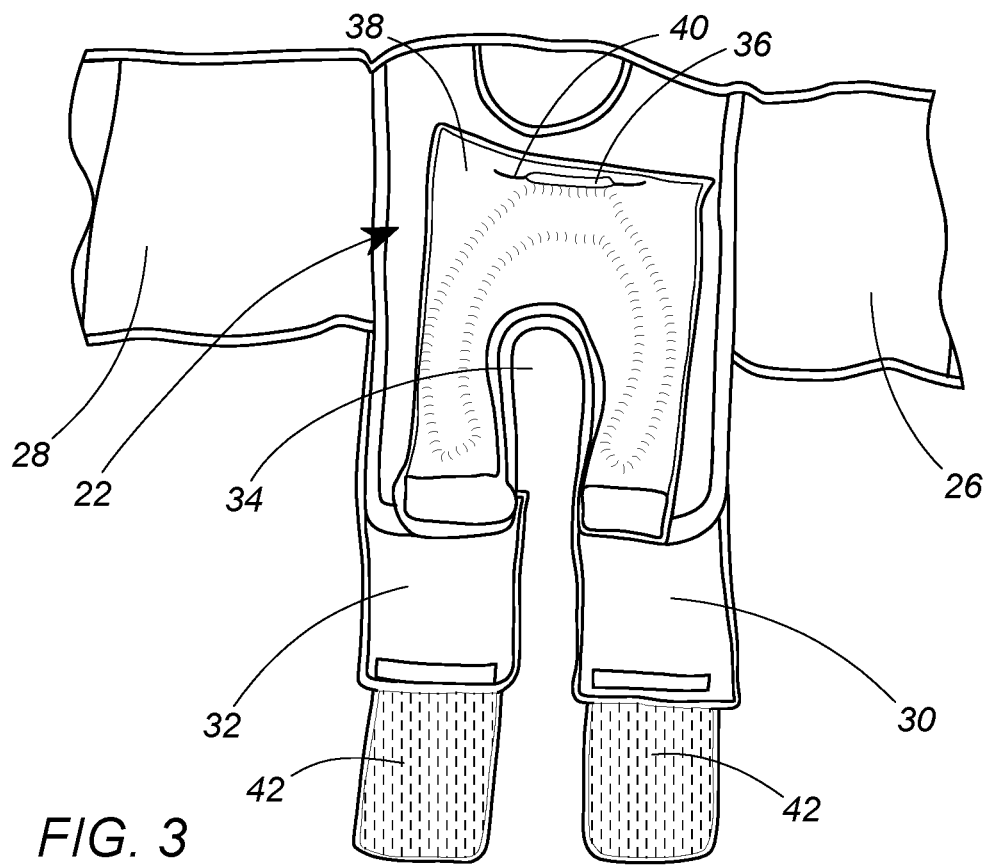
FIG. 3 is a drawing of another aspect of the present disclosure showing an inner view of the upper member.

Referring to FIG. 1, FIG. 2 and FIG. 3, a non-limiting embodiment of the present disclosure is depicted. One embodiment of the present disclosure includes an apparatus for the knee 44 comprising an upper member 20 and a lower member 100. Preferably upper member 20 and lower member 100 are made of any suitable flexible and stretchable material. Such materials may include any elastomeric material that is able to resume its original shape when a deforming force is removed. Examples of such materials include natural rubber and synthetic rubbers, such as neoprene. Note that such examples are illustrative rather than limiting, as any material suitable to one of ordinary skill in the art may be used.

Upper member 20 includes an inner surface 22 and an outer surface 24. When the apparatus is mounted on a leg, inner surface 22 contacts the leg. Upper member 20 further includes a first flap 26 and a second flap 28. First flap 26 is located opposite second flap 28. The upper member 20 is arranged and constructed so that first flap 26 and second flap 28 may be wrapped around a leg to secure the upper member 20 to the leg. First flap 26 may be secured to second flap 28 by use of any suitable fastener, such a hook and loop fasteners, buttons, zippers or any other fastener suitable for securing first flap 26 and second flap 28 to one another. Alternately and not shown in the figures, the upper member can be arranged and constructed to be a sleeve like structure, so as to allow it to be slipped onto the leg and positioned above the knee.

Upper member 20 also includes a first tensioning member 30 and a second tensioning member 32. As shown in FIG. 1 and FIG. 3, the first tensioning member 30 and second tensioning member 32 depend downwardly and define an opening 34. Opening 34 is arranged and constructed to expose a front part of a knee, such as the knee-cap, when the upper member 20 is installed on a leg. Typically, opening 34 includes a top end 50, which may be oval or circular in shape, although any shape suitable as understood by one of ordinary skill falls within the scope of the present disclosure.

Alternatively, a single tensioning member (not shown) falls within the scope of this disclosure. The single tensioning member depends in a downward direction and also defines an opening arranged and constructed to expose a front part of a knee, such as the knee-cap, when the upper member is installed on a leg.

Figure 4:
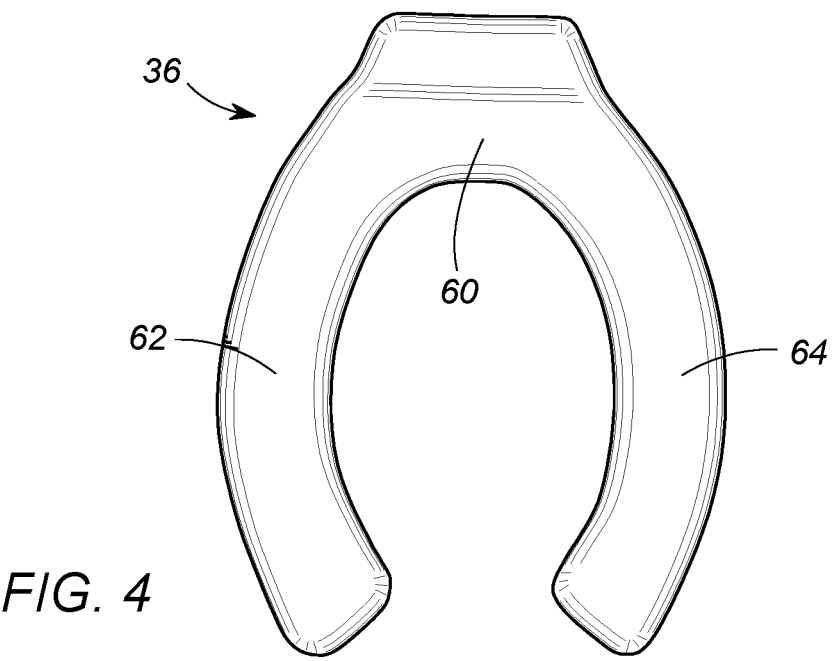
FIG. 4 is a drawing of another aspect of the present disclosure showing a view of the patella biasing device.

Referring now to FIG. 3, the apparatus of the present disclosure further includes a patella biasing device 36. The patella biasing device 36 is roughly U-shaped or horse shoe shaped and is secured on the inner surface 22 of upper member 20 such that the patella biasing device borders opening 34. More particularly, and referring to FIG. 4, the patella biasing device 36 includes head 60, first leg 62 and opposing second leg 64. First leg 62 and second leg 64 depend downwardly from head 60. When the patella biasing device 36 is secured to the inner surface 22, head 60 borders the top end 50 of opening 34. Further, first leg 62 and second leg 64 border opening 34 and run roughly parallel to the first and second tensioning members 30 and 32.

The patella biasing device 36 may be secured to the inner surface 22 in any manner sufficient to accomplish its purpose. That is, when the apparatus of the present disclosure is mounted on the leg, one of the purposes of the patella biasing device is to bias a patella in a downward direction resulting in stretching of the quadriceps muscle. For example, in one embodiment, a receptacle 38 is secured to the inner surface 22. The receptacle 38 is arranged and constructed to border the opening and to serve as a pouch for the patella biasing device 36. That is, the receptacle 38 secures the patella biasing device on the inner surface 22. In the embodiment shown in FIG. 3, the patella biasing device may be removed from the receptacle and re-installed in the receptacle through a slit 40 in the upper end of receptacle 38.

As discussed above, the patella biasing device 36 may be located on the inner surface 22 so as to border opening 34. Once in place, the receptacle 38 may be placed over or around the patella biasing device to secure it to the inner surface 22. Such an embodiment would not necessarily include a slit. Moreover, any other method known to one of ordinary skill may be employed to secure the patella biasing device 36 to the inner surface 22. For example, an adhesive or thread may be used to secure the patella biasing device directly to the inner surface.

Referring to FIG. 2, the apparatus of the present disclosure further includes a flexible lower member 100 arranged and constructed to encircle the leg below the knee. One embodiment includes a first lower member flap 110 with an upper tab 120 and a lower tab 130. Second lower member flap 140 includes second upper tab 150 and second lower tab 160. First lower member flap 110 and second lower member flap 140 are located on opposing sides of lower member 100 and are designed and constructed to wrap around the leg and fasten together to secure the lower member to the leg.

Any appropriate fastener may be used. Referring to FIG. 2, a hook and loop fastener is employed. Hook sections 170 and 180 are located on second upper tab 150 and second lower tab 160 respectively. An additional hook section 190 may be included to accommodate a larger range of leg sizes. Opposing loop sections (not shown) are located on upper tab 120 and a lower tab 130 of first lower member flap 110.

In operation, first lower member flap 110 is wrapped around the knee and secured to second lower member flap 140 via the fastening system described above. It should be understood that any other fastening system may be employed to secure lower member 100 to the leg as would be understood by one of ordinary skill in the art. Alternatively, and not shown in the figures, lower member 100 may be arranged and constructed to be a sleeve like structure, so as to allow it to be slipped onto the leg and positioned below the knee.

The apparatus includes a fastening system to connect the upper member 20 with lower member 100. The fastening system is arranged and constructed to connect the upper and lower members. And, when the apparatus is mounted on the leg, the fastening system is arranged and constructed to create a downward force against the patella via the patella biasing device, which results in stretching the quadriceps muscle that is connected to the patella.

Now referring to FIG. 2 and FIG. 3, the apparatus includes an upper member to lower member fastening system comprising hook sections arranged and constructed to mate with opposing loop sections system. As shown in FIG. 3, hook sections 42 are located near the bottom of first tensioning member 30 and second tensioning member 32. Alternatively, and not shown, one section of hooks may be used in the embodiment comprising a single tensioning member.

Figure 5:
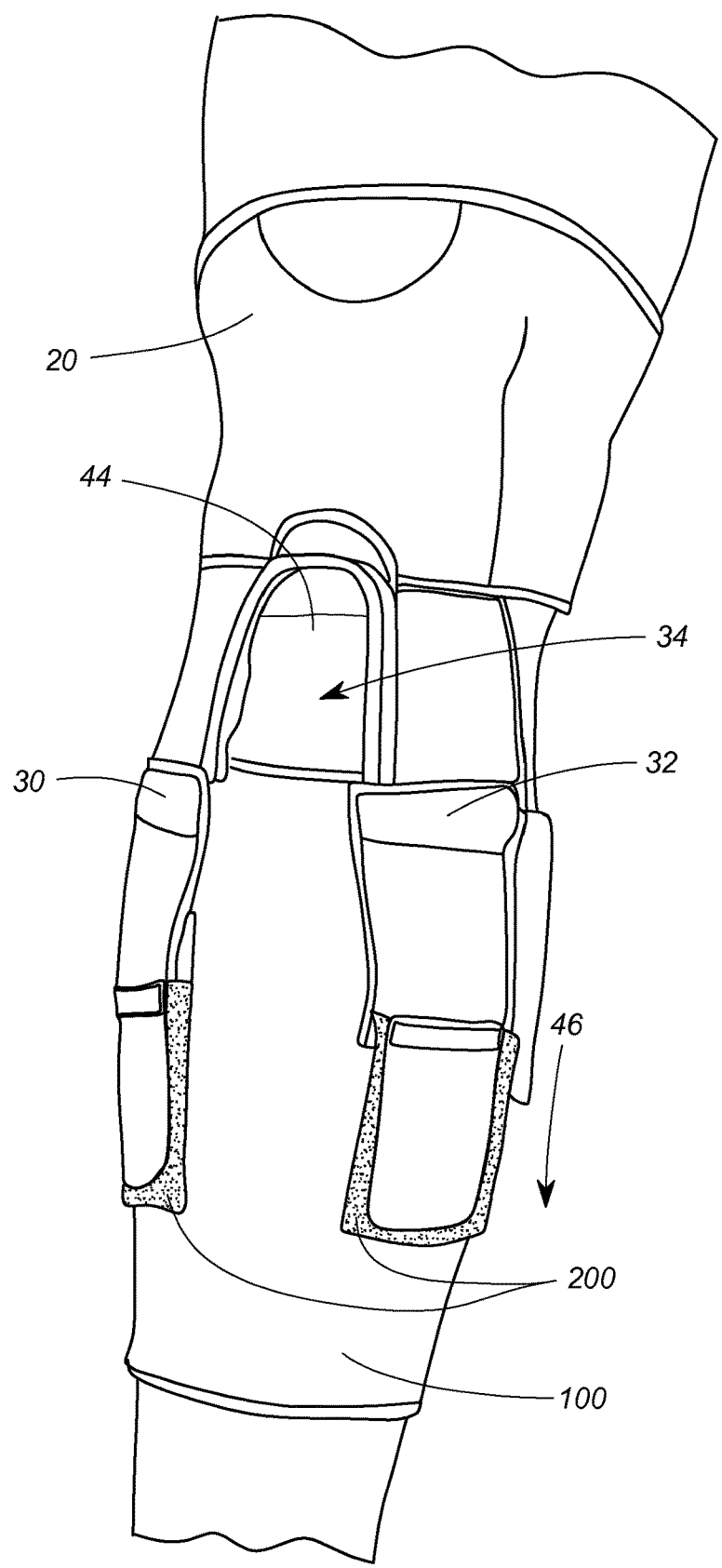
FIG. 5 is another aspect of the present disclosure showing an apparatus for the knee positioned on a knee.

Now referring to FIG. 2, one or more loop sections 200 are located on lower member 100. The one or more loop sections 200 will be located on the lower member 100 as appropriate to facilitate mating with the one or more hook sections 42. Referring to FIG. 5, when the upper member 20 is mounted on the leg above the knee 44 and lower member 100 is mounted on the leg below the knee 44, tensioning members 30 and 32 are stretched in a downward direction 46 toward the lower member 100 and hook sections 42 are attached to receiving loop sections 200. The stretching of the tensioning members biases the patella biasing device against the top of the patella and positions the patella in such a manner as to create a stretch in the connected quadriceps muscle.

In another aspect of the present disclosure, a method for treating knee pain is disclosed. Such a method may include providing an upper member 20 arranged and constructed to encircle a leg above a knee, the upper member 20 having an outer surface 24, an inner surface 22 and an opening 34 for exposing a front of the knee, at least one tensioning member integral with the upper member and depending downwardly therefrom. The upper member 20 further includes a patella biasing device 36 secured on the inner surface 22 of the upper member. The patella biasing device 36 is arranged and constructed to border the opening 34, as previously described. The method further includes the step of attaching the upper member 20 around the leg such that the opening 34 is positioned to expose the front of the knee and the patella biasing device 36 is positioned in close proximity to a patella.

The method also includes providing a lower member 100 arranged and constructed to encircle the leg below the knee and providing a tensioning member fastening system arranged and constructed for connecting the upper member 20 and the lower member 100 via the at least one tensioning member. The method further includes attaching the lower member 100 around the leg below the knee.

Once the upper member 20 and lower member 100 are attached to the leg, the method includes connecting the upper member 20 with the lower member 100 by stretching the at least one tensioning member in a downward direction 46 and attaching the at least one tensioning member 30 and 32 to the lower member 100 via the tensioning member fastening system. When the upper member 20 and lower member 100 are connected, as described herein, the patella biasing device 36 biases the patella in a downward direction resulting in stretching of a quadriceps muscle.

It will be understood by one of ordinary skill in the art that the above description of the method is not limiting with respect to the sequence of the steps disclosed. The sequence of steps can be altered and still fall within the scope of the present disclosure.

The apparatus and method of the present disclosure addresses the short comings associated with prior art knee braces. The apparatus is arranged and constructed in such a manner to provide a biasing force that pulls on the patella and forces a stretch into the quadriceps muscles. With continued use of the disclosed apparatus and method, the quadriceps muscle will lengthen over time and eventually allow the patella to assume its proper position. Thus, short time use of the apparatus disclosed herein alleviates knee pain by positioning the patella in its proper location, while long term use stretches the quadriceps muscle gradually lengthening it to eventually allow the proper and natural positioning of the patella without the use of the disclosed apparatus. Thus, the apparatus and method of the present disclosure provides short term as well as long term relief from knee pain. Moreover, the apparatus of the present disclosure is arranged and constructed such that it may be worn by patients after undergoing ACL surgery. It such cases, the apparatus of the present disclosure will not contact the incision on top of the patella. Users of the present apparatus will be able to exercise the quadriceps muscle to regain neuromuscular control without the range of motion complications that result from tight "quads" and poor patella positioning.

It should be understood that relative positional terms such as "upper," "lower," "inner," "outer," "downward," "front", "back," "top" and the like are with reference to the normal arrangement of the apparatus described herein as it is installed on the leg when the wearer is in the standing position and should not be considered otherwise limiting.

The present disclosure has been described in an illustrative manner. It is to be understood that the terminology that has been employed herein is intended to be in the nature of words of description rather than word of limitation. While there have been described herein, what are considered to be preferred and exemplary embodiments of the present disclosure, other modifications of the disclosure shall be apparent to those skilled in the art from the teachings herein and, it is, therefore, desired to be secured in the appended claims all such modification as fall within the true spirit and scope of the disclosure.

I claim:

1. A method for treating knee pain comprising the steps of:
   providing a flexible upper member arranged and constructed to encircle a leg above a knee, the upper member having an outer surface, an inner surface and an opening having a curved top; the opening arranged to expose a front of the knee, at least one tensioning member integrally formed with the flexible upper member and depending downwardly therefrom, the at least one tensioning member and flexible upper member integrally formed as a unitary structure; a patella biasing device secured on the inner surface and bordering the curved top of the opening;
   providing a flexible lower member arranged and constructed to encircle the leg below the knee, the lower member separate from the upper member when not connected to the upper member;

providing a tensioning member fastening system arranged and constructed for connecting the upper member and the lower member via the at least one tensioning member;

attaching the flexible upper member around the leg such that the opening is positioned to expose the front of the knee and to position the patella biasing device in close proximity to a top of a front of a patella;

attaching the flexible lower member around the leg below the knee; and connecting the flexible upper member with the flexible lower member by stretching the at least one tensioning member in a downward direction and attaching it to the flexible lower member via the tensioning member fastening system so that when the upper member and lower member are connected the patella biasing device biases the patella in the downward direction resulting in stretching of a quadriceps muscle.

2. The method of claim 1 wherein the at least one tensioning member comprises a first tensioning member and a second tensioning member, the first and second tensioning members arranged substantially parallel to one another and located on opposing sides of the opening.

3. The method of claim 2 wherein the flexible upper member is constructed of an elastomeric material.

4. The method of claim 3 wherein the elastomeric material is neoprene.

5. The method of claim 2 wherein the tensioning member fastening system includes a section of hook material located near a lower end of the first tensioning member and second tensioning member and a corresponding section of loop material located on the lower member such that when the hook material is connected to the loop material the first and second tensioning members are stretched creating a downward biasing of the patella biasing device against the top of the patella resulting in stretching of the quadriceps muscle that is connected to the patella.

6. The method of claim 1 further comprising a receptacle located on the inner surface, the receptacle bordering the opening and arranged and constructed to secure the patella biasing device along the curved top of the opening.

7. An apparatus for treating knee pain comprising:

an upper member having an inner surface and an outer surface, a first flap and a second flap, the first flap and second flap located on opposite sides of the upper member and constructed and arranged to wrap around a leg above a knee and be secured to one another, the upper member further including a first tensioning member arranged parallel to a second tensioning member, the first and second tensioning members defining an opening there between and configured for exposing a front portion of the knee, the opening having a curved top, the first tensioning member and the second tensioning member depending in a downward direction;

a patella biasing device secured on the inner surface and bordering the curved top of the opening;

a lower member arranged and constructed to encircle the leg below the knee, the lower member separate from the upper member when not connected to the upper member; and a fastening system arranged and constructed for connecting the upper member to the lower member by securing the first and second tensioning members to the lower member such that when the upper member and lower member are configured to be mounted on the leg and connected via the fastening system, the patella biasing device is configured to position a patella of the knee so as to stretch a quadriceps muscle of the leg; and wherein the flexible upper member, first tensioning member and second tensioning member are integrally formed as a unitary structure such that the first and second tensioning members cannot be separated from the flexible upper member without deconstructing the flexible upper member.

8. The apparatus of claim 7 wherein the fastening system includes a hooks section located near a lower end of the first tensioning member and a second hooks section located near a lower end of the second tensioning member and at least one corresponding loops section located on the lower member such that when the hooks sections are connected to the at least one loop section the first and second tensioning members are configured to be stretched creating a downward biasing of the patella biasing device against a top of the patella resulting in stretching of the quadriceps muscle that is connected to the patella.

9. The apparatus of claim 8 wherein the upper member is constructed of a flexible material.

10. The apparatus of claim 9 further comprising a receptacle located on the inner surface, the receptacle bordering the opening and arranged and constructed to secure the patella biasing device.

11. The apparatus of claim 7 wherein the patella biasing device includes a head bordering the curved top, a first leg depending downwardly from the head, an opposing second leg depending downwardly from the head, the first leg and second leg arranged substantially parallel to the first and second tensioning members.

12. An apparatus for a knee comprising:

a flexible upper member arranged and constructed to encircle a leg above a knee, the upper member having an outer surface, an inner surface, at least one tensioning member depending downwardly therefrom and an opening for exposing a front of the knee;

a patella biasing device secured on the inner surface and bordering the opening;

a flexible lower member arranged and constructed to encircle the leg below the knee, the lower member separate from the upper member when not connected to the upper member; and at least one tensioning member fastening system arranged and constructed for connecting the upper member and the lower member via the at least one tensioning member such that when the upper member and lower member are configured to be mounted on the leg and connected via the at least one tensioning member fastening system, the at least one tensioning member is stretched creating a downward biasing of the patella biasing device;

wherein the at least one tensioning member is a continuous extension of the flexible upper member.

13. The apparatus of claim 12 wherein the at least one tensioning member fastening system includes at least one hook section and at least one opposing loop section located on the at least one tensioning member and the lower member, wherein when the at least one hook section is connected to the at least one loop section, the at least one tensioning member is stretched and configured for creating a downward biasing of the patella biasing device against a patella resulting in stretching of a quadriceps muscle that is connected to the patella.

14. The apparatus of claim 13 wherein the flexible upper member is constructed of an elastomeric material, the at least one tensioning member defining the opening, the opening having a curved top, and the patella biasing device bordering the curved top.

15. The apparatus of claim 14 further comprising a receptacle located on the inner surface, the receptacle bordering the opening and arranged and constructed to secure the patella biasing device.

16. The apparatus of claim 12 wherein the at least one tensioning member comprises a first tensioning member and a second tensioning member, the first and second tensioning members arranged substantially parallel to one another and located on opposing sides of the opening.

\* \* \* \* \*